United States Patent [19]

Petrick

[11] Patent Number: 5,935,362
[45] Date of Patent: Aug. 10, 1999

[54] METHOD FOR MANUFACTURING IMPROVED SELF-SEALING INJECTION SITES AND PLUGS

[75] Inventor: Timothy B. Petrick, Brooklyn Park, Minn.

[73] Assignee: Mentor Corporation, Santa Barbara, Calif.

[21] Appl. No.: 08/927,327

[22] Filed: Sep. 11, 1997

Related U.S. Application Data

[62] Division of application No. 08/739,617, Oct. 30, 1996, Pat. No. 5,725,507, which is a continuation of application No. 08/205,995, Mar. 4, 1994, abandoned.

[51] Int. Cl.[6] .................................................. B32B 31/00
[52] U.S. Cl. ......................... 156/165; 156/161; 156/162; 156/172; 156/185; 156/229
[58] Field of Search .................... 156/161, 162, 156/165, 172, 185, 229

[56] References Cited

U.S. PATENT DOCUMENTS

| | | | |
|---|---|---|---|
| 2,360,925 | 10/1944 | Wyman | 156/165 |
| 2,584,501 | 2/1952 | Roberts | 156/165 |
| 3,194,273 | 7/1965 | De Laubarede | 156/229 |
| 3,231,442 | 1/1966 | Michael | 156/165 |
| 3,600,718 | 8/1971 | Boone | 3/36 |
| 3,883,902 | 5/1975 | Lynch | 3/36 |
| 3,919,724 | 11/1975 | Sanders | 3/36 |
| 3,974,012 | 8/1976 | Hogarth | 156/165 |
| 4,138,285 | 2/1979 | Michael | 156/165 |
| 4,155,791 | 5/1979 | Higuchi | 156/165 |
| 4,190,040 | 2/1980 | Schulte | 128/1 R |
| 4,216,774 | 8/1980 | Graber | 128/296 |
| 4,217,889 | 8/1980 | Radovan | 128/1 R |
| 4,263,682 | 4/1981 | Bejarano | 3/36 |
| 4,329,193 | 5/1982 | Sznopek et al. | 156/165 |
| 4,350,549 | 9/1982 | Frehner | 156/162 |
| 4,428,364 | 1/1984 | Bartolo | 128/1 R |
| 4,685,447 | 8/1987 | Iversen | 128/1 R |
| 4,738,657 | 4/1988 | Hancock | 604/93 |
| 4,773,908 | 9/1988 | Becker | 623/8 |
| 4,798,584 | 1/1989 | Hancock | 604/93 |
| 4,834,720 | 5/1989 | Blinkhorn | 604/244 |
| 4,840,615 | 6/1989 | Hancock | 604/93 |
| 4,857,053 | 8/1989 | Dalton | 604/93 |
| 4,955,906 | 9/1990 | Coggins | 623/8 |
| 4,955,907 | 9/1990 | Ledergerber | 623/8 |
| 4,969,899 | 11/1990 | Cox | 623/8 |
| 5,047,104 | 9/1991 | Preis et al. | 156/165 |
| 5,137,529 | 8/1992 | Watson | 604/891.1 |
| 5,139,841 | 8/1992 | Makoui | 428/109 |
| 5,141,508 | 8/1992 | Bark | 623/8 |
| 5,354,275 | 10/1994 | Behnke | 604/86 |
| 5,403,293 | 4/1995 | Grabenkort | 604/256 |

FOREIGN PATENT DOCUMENTS 2816883 10/1978 Germany .

*Primary Examiner*—David A. Simmons
*Assistant Examiner*—Robert R. Koehler
*Attorney, Agent, or Firm*—Fish & Richardson P.C., P.A.

[57] ABSTRACT

Small compression type injection site in the form of a self-sealing septum-like member that is self-sealing for hypodermic needle punctures and the like and a method of manufacture. Compressive stresses are introduced into a stretched elastomeric rod, whereby the decreased diameter cross section is maintained by placing a wrapping around and about the stretched rod and adhesively sealing it thereto. Sliced cross-sectional pieces of the rod then provide injection sites to be incorporated into the wall of an implantable prosthesis as by bonding or the like.

17 Claims, 3 Drawing Sheets

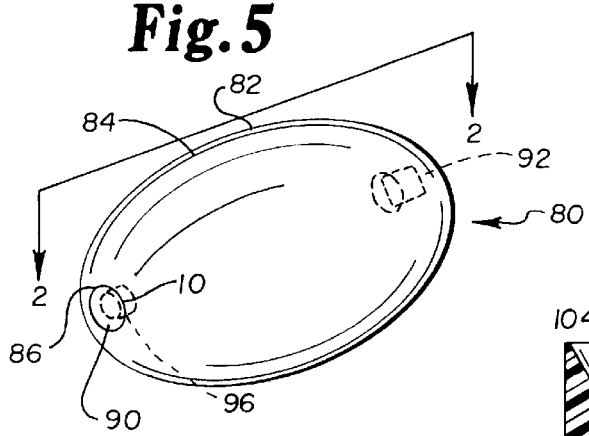
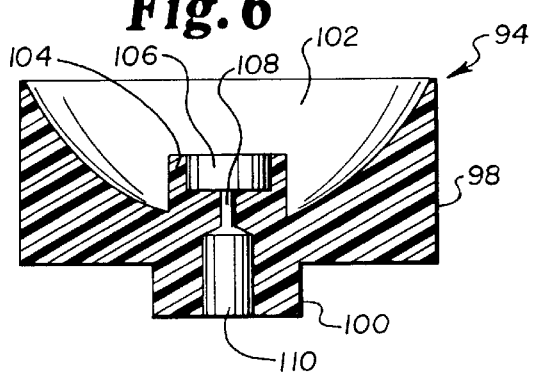
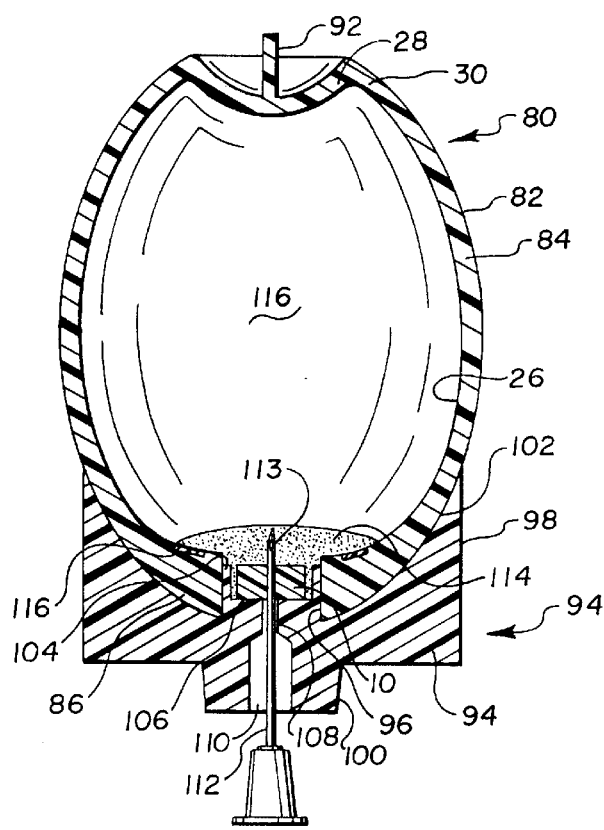
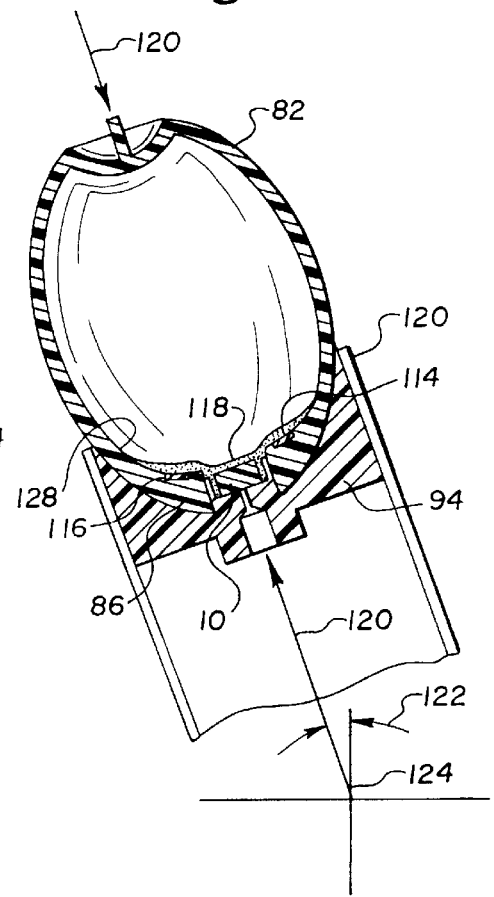

METHOD FOR MANUFACTURING IMPROVED SELF-SEALING INJECTION SITES AND PLUGS

This is a divisional of application Ser. 08/739,617, filed Oct. 30, 1996, now U.S. Pat. No. 5,725,507, which is a continuation of application Ser. No. 08/205,995, filed Mar. 4, 1994, now abandoned, and hereby claims the benefit of filing date priority under 35U.S.C. §120 from such applications.

BACKGROUND OF THE INVENTION

This invention pertains to improved compression type self-sealing injection sites, and more particularly, it relates to a minimum size self-sealing injection sites or septums featuring self-sealing subsequent to puncture by a hypodermic needle or the like. The term "injection site" as used herein refers to self-sealing systems and similar bodies of the prior art used as ports and plugs. The injection sites of the invention have particular application in implantable prosthetic devices of the type which require filling through the site with a fluid by means of an injection needle or the like. For example, penile prosthesis, mammary prosthesis or tissue expanders devices having remote injection sites and drug delivery systems will make use of the improved injection sites of this invention. This invention was developed for use with a saline filled testicular prosthesis which is described herein. However, the injection sites of this invention can be used in any device requiring a plug or septum.

Injection sites, buttons and other self-sealing septums of the prior art using compression to self-seal are described in U.S. Pat. Nos. 4,428,364; 4,738,657; 4,798,584; 4,840,615; and 5,137,529.

The injection site of U.S. Pat. No. 4,428,364 contains multiple layers of fabric reinforced silicone rubber sheets fabricated into a dome shaped wall. The fabric weave within the layers is oriented in different directions. The reinforced silicone sheets are subjected to a swelling agent. The combined effect of the swelling silicone and restraining fabric causes a compressive stress to develop in the wall.

The injection sites described in U.S. Pat. Nos. 4,738,657, 4,798,584, and 4,840,615 are all generally similar. They use various bending and inverting techniques to create compressive stresses on the inside surface of the outer wall of the site. Compression is developed by (1) bending a sheet of silicone into a domed shape; (2) inverting a previously formed silicone dome; and (3) cutting the wall of a silicone tube then rolling it into a flat sheet.

Compression is attained in U.S. Pat. No. 5,137,529 through interference fits. An elastomeric septum formed with the outer housing is compressed by a rigid base member.

The prior art discussed above all develop enough compression to self-seal when subjected to hypodermic needle punctures. However, the prior art depends on other rigid members to maintain compression.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

SUMMARY OF THE INVENTION

This invention provides new and improved compression type self-sealing injection sites and a method of manufacturing such sites. Generally, an injection site is provided in which energy has been stored by means of a wrapping associated with the site body. Specifically in one embodiment of this new site, compressive stresses are induced in an elastic elastomeric rod such as silicone by stretching the rod, causing its diameter to decrease. A strand, preferably a continuous one, such as fiberglass filament, is then wound around the stretched rod. The strand maybe passed through an adhesive prior to the winding step or exposed to it after winding. The wrapping associated with the rod stores the energy produced by stretching of the rod when the tension is released. Individual injection sites are formed by cutting or slicing the rod transversely to desired lengths after the adhesive cures.

More specifically, the present invention provides an increased density injection site in which a decreased cross section is maintained by an adherent wrapping about a stretched elastomeric rod which is subsequently cut into appropriate cross-sectional lengths to provide discrete injection sites. One such site may then be bonded into an orifice in the wall of an implantable prosthesis for sealing the contents thereof and to act as a self-sealing injection site or septum.

Consequently, the present invention provides plugs and compression type injection sites that are self-sealing to hypodermic needle punctures and the like and a method of manufacturing same. The compressive stresses are induced into an elastomeric rod, such as an elastic silicone rod, by stretching the rod, causing the diameter to decrease. A wrapping such as a fiberglass strand impregnated with silicone adhesive, is wound around the stretched rod and allowed to cure. A plurality of minimum size injection sites can be formed from the rod by cutting it to desired lengths after the adhesive has cured and the tension has been released from the rod.

The injection sites of the present invention may be used, for example, for introduction of a physiologically safe fluid, such as saline into a testicular prosthesis. It also has uses in other prosthetic devices. For example, penile prosthesis, mammary prosthesis, and tissue expanders and so forth as already mentioned.

According to a preferred embodiment of the present invention, there is provided a compression type injection site having a central elastic silicone member in the form of a slug held in an elongated and compressed form by a fiberglass filament wound about and adhered to the outer circumferential surface of the central elastic silicone slug.

One significant aspect and feature of the present invention is that the injection sites have a precompressed central member bound by a wrapping or the like.

An additional significant aspect and feature of the present invention is that the injection sites have minimum size, both diameter and thickness, and minimum palpability or awareness when carried by an implanted prosthesis.

Yet another significant aspect and feature of the present invention is that the injection site flexibility contributes to the continuity of the prosthesis in which it is carried.

Also, the wrapping arrangement about the core presents a good bonding surface for mounting the injection sites of this invention into the device which is to make use of them.

The precompressed arrangement of these injection sites stores energy therein for improved self-sealing and eliminates the need for rigid supporting members. Thus, they can be very small, both in diameter and length.

Other significant aspects and features of the present invention include enhanced fatigue resistance and enhanced adhesion to a flexible member of a prosthesis.

It is a general object of this invention to provide improved injection sites and a method of manufacturing same, especially for use in implantable prostheses, although they may be used wherever such sites have been used in the past as a self-sealing septum or as a plug.

BRIEF DESCRIPTION OF THE FIGURES

Other objects of the present invention and many attendant advantages will be readily appreciated as it becomes better understood by reference to the following detailed description when considered in connection with the accompanying drawings, in which like reference numerals designate like parts throughout the Figures thereof and wherein:

FIG. 5 illustrates a perspective view of a testicular prosthesis, incorporating the present invention;

FIG. 6 illustrates an alignment fixture;

FIG. 7 illustrates the method of injecting adhesive into the interior of the elastomeric shell:

FIG. 8 illustrates the elastomeric shell being rotated off vertical to form an evacuation dome;

DETAILED DESCRIPTION OF THE PREFERRED EMBODIMENTS

Figure 1:
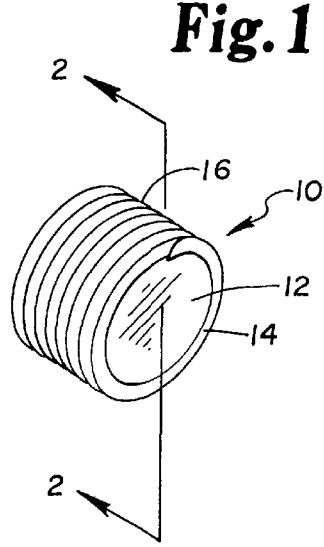
FIG. 1 illustrates a perspective view of an injection site of, the present invention.

FIG. 1 illustrates a perspective view of a preferred injection site 10 according to the invention having a central elastomeric silicone core or slug 12 wrapped and bound in compression by a fiberglass strand 14 in the form of a coil or wrapping 16. Other suitable elastomeric materials may be used as well. The fiberglass strand 14 is preferably impregnated with adhesive which adheres to the outer circumferential surface of the elastomeric silicone core 12. The adhesive coating when cured causes adjoining tangential areas of the fiberglass continuous coil 16 to mutually adhere to each other and provide for maximum holding strength. In the alternative, strand 14 may be wound tightly enough for adjacent portions of the strand to overlap each other or multiple layers of strand may be provided, thus creating a continuous wrapping of fiberglass coated with adhesive.

Also, in the alternative, wrapping 16 may comprise a metal winding as of fine wire or may even comprise a single flat piece of metal in a ring shape or the like tightly encompassing the entire peripheral area of body 12 under compression. Furthermore, the outer surface may be roughened, as by etching or the like, to adapt it for improved sealing engagement or contact.

Figure 2:
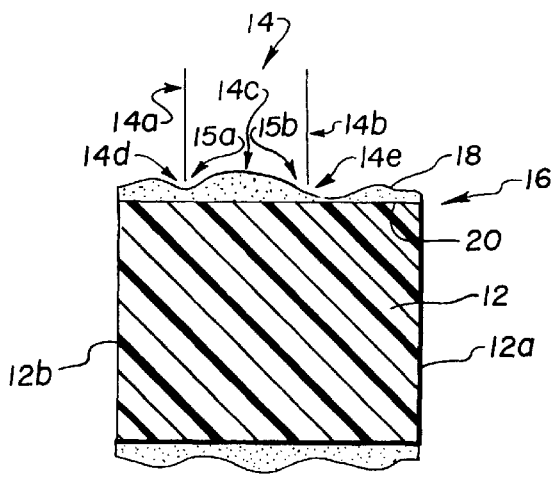
FIG. 2 illustrates a cross-sectional view along line 2—2 of FIG. 1.

Referring now to FIG. 2, this Figure is a cross-sectional view along line 2—2 of FIG. 1 in which all numerals correspond to those elements as previously described in FIG. 1. Illustrated in particular is the elastomeric silicone core or slug 12, the diameter of which has been previously reduced from a larger diameter to a smaller diameter by stretching its predecessor rod to thereby place body 12 under compression and also to increase its density as later described in detail. The Owens Corning fiberglass strand 14 a synthetic fiber, having a nominal diameter of 0.0065 inches by way of example and for purpose of illustration only, is constructed of a great number of fiberglass filaments, two filaments 15a–15b of which are shown is FIG. 2, and is impregnated with a medical grade adhesive 18 such as Raumedic medical grade adhesive (SI 1511). The adhesive is applied under tension. Owens Corning 408 fiberglass filaments 15a–15b, by way of example and for purposes of illustration only, make up the fiberglass strand 14 and are presently preferred. This is a continuous filament yarn (Yarn No. ECD 225 110) of approximately nominal yards per pound—22,500, 3.0 lbs. an average breaking strength and an approximnate diameter of 0.0065 inches, Denier equivalent 198 and has the following designation ECD 115 110 636. It is available from LM Specialty Yarns, Owens Corning Fiberglass, Fiberglass Tower, Toledo, Ohio 43659. The strand could also be polyester terephthalate or other suitable synthetic material, or natural fibers such as silk, cotton, etc. or metal, as already discussed above.

The term "strand" is used herein in a generic sense to include simple fibers, filaments, multi-fibers, multi-filaments and the like whether of synthetic, natural or metallic nature, including gold, silver, stainless steel and the like.

The fiberglass adhesive impregnated strand 14; which nominally is round, is lubricated by the adhesive 18 and assumes a flattened profile spanning the distance as designated by arrows 14a–14b in FIG. 2 with the bulk of the filaments 15a–15b being aligned at a peak 14c which tapers off to include a lesser amount of filaments 15a–15b at each side of the peak in valleys 14d and 14e. The medical grade adhesive 18 impregnated into the strands 14 mutually bonds the fiberglass filaments 15a–15b of each flattened strand 14 to themselves and to the adjacent turns of the strand 14 which forms the homogenous surrounding coil 16 about the elastic silicone core 12. The adhesive also bonds fiberglass filaments 15a–15b to the elastic silicone core 12. The flattened profile of the fiberglass filaments 15a–15b impregnated and adhered to each other about the elastic silicone core 12 presents when cured a suitable outer bonding surface for adhesively bonding and securing the injection site within the bore, opening or other orifice into which the injection site is to be incorporated. For example, in a preferred form it will be incorporated into an implantable prosthesis which may be, but not limited to, tissue expanders, mammary prostheses, prostheses used for fluid infusion or prostheses used for drug delivery. Also, the injection site may be inserted as a lumen plug in a prosthesis or other device.

Considering the injection site as shown in FIGS. 1 and 2, it is seen that an elastomeric core 12, preferably in a slug-like configuration is provided having opposite surfaces 12a and 12b interconnected by a peripheral edge or circumferential surface 20. The body is held in compression by a tight wrapping around surface 20 which is preferably held in place by a suitable adhesive, the wrapping being accomplished when core 12 is in tension.

Figure 3:
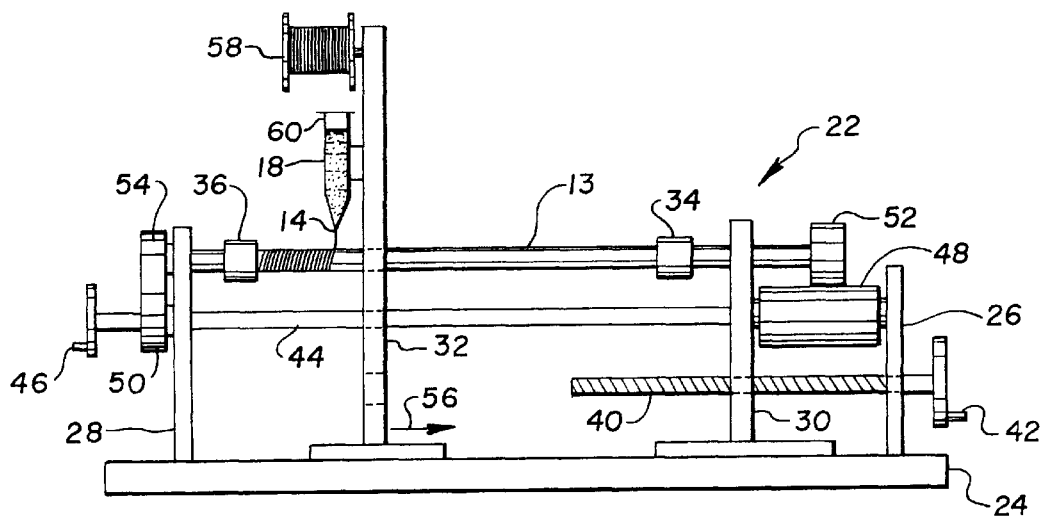
FIG. 3 illustrates a method of application of a wrapping to a stretched rod of elastomeric material in forming an injection site of the invention.

A preferred method of manufacturing such an injection site will now be described with particular reference to FIG. 3. FIG. 3 illustrates a method of application of wrapping 16 to a silicone rod. The numerals referred to in FIG. 3 correspond to those elements previously described.

A fixture generally indicated at 22 includes a base 24, opposing fixed upright supports 26 and 28, and moveable upright supports 30 and 32. An elastic silicone rod 13, for example, may be fashioned by molding or extruding silicone or other elastomer material such as gum rubber, or by molding liquid silicone rubber or other elastomer material. The rod 13 is supported between rotatable clamps 34 and 36 at the upper portion of the fixed support 28 and movable support 30, respectively. A threaded crank rod 40 supported by fixed support 26 is turned by a crank 42 to horizontally position movable support 30, thus causing rod 13 to be stretched and elongated between the rotatable clamps 34 and 36. This stretching and elongating causes rod 13 to be put under tension and to decrease the profile cross-section or diameter of the rod. This decrease in diameter provides a source of cores 12 for the injection sites of the invention which causes inflation needle punctures to be self-sealing. This compaction resulting from tension is held in reduced cross-section by the application of an adhesive impregnated wrapping 16 which is preferably a closely wound strand of fiberglass in a closely spaced form about the outer periphery of the stretched and elongated rod 13 and which may be distributed over most of the length thereof. A threaded rod, crank and gear assembly advances movable support 32 to apply an adhesive impregnated strand 14 over, around and about the stretched and elongated rod 13. The strand winding process may be automated. A threaded crank rod 44 having a crank 46 is supported by the opposing fixed supports 26 and 28. Gears 48 and 50 align over and are fixed to the threaded crank rod 44 for rotation by it upon rotation of crank 46. Gears 52 and 54 are supported for rotation at the upper ends of fixed support 28 and movable support 30 and are also attached to the rotatable clamps 34 and 36, respectively. Gear 50 meshes with gear 54 and gear 52 meshes with and slidingly engages gear 48. Crank 46, when activated, turns the threaded crank rod 44 and gears 48 and 50 directly, and also turns rotatable clamps 34 and 36 at equal rates through the intermeshed gears 52 and 54 to rotate the elongated and stretched rod 13 about its longitudinal central axis.

The action of the crank rod 46 also causes movable support 32 to be horizontally moved and positioned as indicated by arrow 56 to apply the adhesive impregnated strand 14 in a uniform manner around and about the stretched and elongated rod 13 as it rotates between rotatable clamps 34 and 36. A strand source in the form of a spool 58 and an adhesive source container 60 of medical grade adhesive 18 secures to the upper portion of the movable support 32. Spool 58 offers a slight drag so that as the strand is pulled from spool 58 by rotating rod 13 a slight amount of tension is applied to strand 14 so that flattening of the strand will occur. Strand 14 aligns in a perpendicular fashion to the elongated rod 13 as it passes through the source container and as it is wound about rod 13. The strand is wound so as to place the coils thereof as closely together as possible on the rod. Strand 14 is impregnated by the medical grade adhesive 18 as the strand passes through the medical grade adhesive 18 in the adhesive source container 60. Adhesive 18 is then allowed to cure and dry under tension after the strand has been wrapped about rod 13. When the axial tension on rod 13 is released, the rod is then placed under radial compression by the cured winding. The wrapped rod is then cut in lengths for subsequent use as discrete individual injection sites, each of which may be used for placement within the injection orifice of a sealed prosthesis or other device. The self-contained injection site can also be used as a lumen plug in any type of device, medical or other wise. The wrapping presents a bonding surface for bonding the site into an opening in a prosthesis or the like.

The material of rod 13 may include a colorant such as titanium dioxide for visualization or it may include a material such as barium sulfate to render it radiopaque for visualization under radioscopy.

Figure 4:
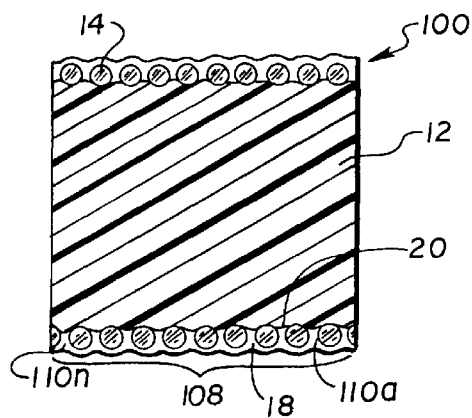
FIG. 4, an alternate embodiment, illustrates a cross-section of an injection site having a monofilament member winding about the circumferential surface thereof.

FIG. 4, an alternative embodiment, illustrates a cross-sectional view of an injection site wound with a monofilament member. Illustrated in particular is an elastic silicone core 12 having a diameter reduced from a larger diameter to compact its diameter and increase its density as previously described. A metallic or plastic that retains its round shape, monofilament or other suitable member 14 laden with a medical grade adhesive 18 is wound under a slight tension about an elastomeric rod as before to provide the elastic silicone core 12 with peripheral winding or wrapping in a manner consistent with the teachings of the previous description of the invention. Alternately, bifilar, monofilament or multiple monofilaments members of synthetic, natural or metallic material may be used. Also, the wrapping need not be parallel when bifilar or the like but may be helical and so forth. Adhesive 18 adheres in a plurality of areas and along a series of points and provides for maximum holding power of the wrapping. The continuous spread of adhesive 18 over the peripheral surface 20 provides continuous adhesion of the filament member 14 to itself and to the elastomer rod/core, thus forming a semi-rigid casing like member. The medical grade adhesive 18 flows and bridges across the spaces between the winding to encapsulate coil member 14. Curing is accomplished under tension. The assembly is then cut to appropriate lengths for incorporation into an implantable device as individual injection sites. The bonding of the turns of coil 14 to itself and the bonding of the turns of coil 14 to the elastic silicone core 12 provides maximum bondage and adherence to forcibly maintain and contain the stretched elastic silicone core 12 under radial compression at its desired decreased diameter (as compared to its source rod) which insures sealing of a syringe needle puncture or the like subsequent to syringe needle withdrawal from the injection site.

EXAMPLES

In a preferred embodiment injection sites have been made from Dow Corning Q7-4735 silicone elastomer. An equivalent material is MED-4735 from the Nusil Technology Company. Six to ten inch length molded or extruded rods of initial diameter 0.230 inches were stretched until their initial diameter decreased by about 17% i.e., to a diameter of about 0.190 inches. Fiberglass filament was then passed through Raumedic medical grade adhesive (SI 1511) wrapped about the stretched rods while in their tensioned state. The rod was then sliced into 0.090 inch lengths after the adhesive cured to provide a plurality of sites or plugs according to the invention.

Care should be taken to avoid too small a slice of the rod in forming the septum/site as it may deform under the stress. Using the aforementioned materials, for example, it was determined that a 0.250 inch diameter rod stretched down to 0.190 inches and then sliced to 0.080 inch thick slices tended to be unstable and to deform or bow. On the other hand, 0.230 inch rods stretched to 0.190 made stable septum/sites of 0.090 to 0.100 inches thick. Obviously, in the case of any particular materials and sizes, same minor "cut and try" may be necessary. Generally speaking, the amount of compression will determine the length of the injection site—more compression requires greater length.

As already mentioned, this invention was developed to be used primarily in a saline filled testicular prosthesis.

A testicular prosthesis shown in FIG. 5, is an example of a hollow device having a chamber to be closed by a self-sealing septum or plug. Such a prosthesis may comprise a shell as is shown in FIG. 5. More specifically, FIG. 5 illustrates a perspective view of a testicular prosthesis generally indicated at 80 including a shell 82 which is transfer, injection, compression or otherwise suitably molded from a silicone elastomer such as Dow Q7-4840 or Q7-4735 or equivalent material. The elastomeric shell 82 is preferably elliptical in longitudinal cross section to replicate the shape of a testicle and is of a circular transverse cross section. Shell 82 can be produced in a number of sizes to accommodate the proper testicle size and may be filled any desired tension or feel. The elastomeric shell wall is approximately 0.030 inches thick on the sides 84 for purposes of example and illustration only, and increasingly tapers to a thickness of 0.170 inches at one end 86 to accommodate a self-sealing injection site of the invention 10. The self-sealing injection site 10 is bonded in the opening which is carried in an opening 96 in the shell by a medical grade adhesive 90 and aligned thereto prior to bonding as described later in detail. A self-presenting suture tab 92 aligns at the opposing end for securement of the shell 82 to the scrotum or other convenient attachment point.

The injection site is bonded to the shell with the help of an assembly fixture shown in FIG. 6. The fixture locates the injection site in the center of the wall cavity leaving space for 0.025 inch of adhesive circumferential around, and 0.050 inches of adhesive over the injection site. Silicone adhesive, thinned with xylene, is injected through the fixture, or through the injection site, to a depth of about 0.030 inches. The adhesive is allowed to cure 24 hours then the shell and injection site are pulled away from the fixture. The top of the injection site is then covered with adhesive.

More specifically, FIG. 6 illustrates a fixture generally indicated at 94 for alignment of the self-sealing injection site 10 concentrically with the cylindrical bore 96 of the thick end 86 of the elastomeric shell 82 where all numerals correspond to those elements previously described. The fixture 94 includes generally a number of radiused portions including an upper radiused body portion 98 and a lower radiused body portion 100. A cavity 102 conforming to the thick end 86 of the elastomeric shell 82 aligns centrally in the upper radiused body portion 98 for subsequent alignment with the same as illustrated in FIG. 7. Another radiused portion 104 extends upwardly into the region of the cavity 102 to closely align within the cylindrical bore 96 of the elastomeric shell thick end 86 as illustrated in FIG. 7. Three bores 106, 108 and 110 align axially either partially or fully in the radiused portion 104, the upper radiused body portion 98 or the lower radiused portion 100 as illustrated. Bore 106 accommodates the self-sealing injection site 10 and bores 108 and 110 accommodate a fill needle 112 as illustrated in FIG. 7.

FIG. 7 illustrates the method of injecting medical grade adhesive 114 into the interior 116 of the elastomeric shell 82 where all numerals correspond to those elements previously described. The elastomeric shell 82 is aligned in the conforming shaped cavity 102 of the fixture 94. The radiused portion 104 of fixture 94 aligns centrally within the cylindrical bore 96 of elastomeric shell 82. The self-sealing injection site 10 which is placed in the upper bore 106 prior to alignment of the elastomeric shell 82 with fixture 94 is also centrally aligned within the cylindrical bore 96. When alignment has been accomplished, a non-coring needle 112 having one or more ports 113 and having a source of thinned medical grade adhesive 114 attached thereto is inserted through the bores 110 and 108 and through the self-sealing injection site 10. Adhesive 114 then enters the lower region of the elastomeric shell 82 about and above the vicinity of the bore 96 as illustrated so that adhesive 114 covers the lower inner region of the elastomeric shell 82, the serialization and identification area 116, and the top surface of the self-sealing injection site 10. The needle 112 is then withdrawn from the fixture 94 and elastomeric shell 82 and fixture 94 are slowly rotated and are progressively tipped during rotation to allow the adhesive 114 to puddle in an annular fashion around the center portion to form the evacuation dome 118 as illustrated in FIG. 8. The adhesive is then allowed to cure after formation of evacuation dome 118. After curing, fixture 94 is withdrawn from engagement with the elastomeric shell 82 leaving the self-sealing injection site 10 concentrically aligned within the cylindrical bore 96 and adhered to the lower region of the elastomeric shell 82 by the interceding medical grade adhesive 114 as illustrated in FIG. 9.

FIG. 8 illustrates the elastomeric shell 82 being rotated about an axis 120 which is at a variable angle 122 to the vertical 124. The angle 122 generally is 35°, but can include a range of degrees in that several factors such as but not limited to elastomeric shell 82 size, adhesive viscosity, rate of rotation, angle of rotation, temperature, and adhesive setting time will require different angular settings, different rotation speeds, as well as different rates of tipping, other than described herein. A suitable rotatable clamping device 126 slowly rotates the fixture 94 and the contained adhesive laden elastomeric shell 82 at a speed of 4 rpm plus or minus one rpm. The viscous adhesive 114 flows outwardly leaving a shaped evacuation dome 118 centered radially about the axis of the elastomeric shell 82 when shell 82 is tipped-at an angle as now described in detail. The axis of rotation 120 is progressively and slowly tipped over a period of one minute from the vertical axis 124 until reaching the desired angle 122 of about 35° which is the most desirable of angles which can range from about 35 to 55 degrees depending on the size of the elastomeric shell 82 and other factors previously described. During this slow tipping and rotation, adhesive 114 flows from the area over and about the upper area of the self-sealing injection site 10 and along the lower portion of the inner surface 128 to vacate adhesive 114 from the area overlying the self-sealing injection site 10 to form the evacuation dome 118. Alternatively, elastomeric shell 82 can be spun rapidly from about 500 to 1,000 rpm for 10 to 20 seconds, for purpose of example, along the vertical axis to cause the adhesive 114 to flow away from the center to form the evacuation dome 118.

Figure 9:
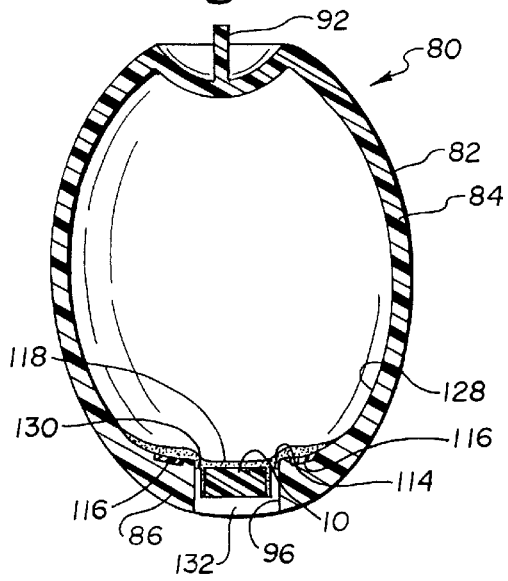
FIG. 9 illustrates the elastomeric shell and self-sealing injection site subsequent to fixture removal.

FIG. 9 illustrates the elastomeric shell 82 and the self-sealing injection site 10 subsequent to removal of the fixture 94 where all numerals correspond to those elements previously described. The self-sealing injection site 10 is suspended concentrically from the adhesive 114 within the cylindrical bore 96. An annular space 130 defined by the annular area between the circumferential surface of the self-sealing injection site 10 and the adjacent walls of the cylindrical bore 96 and another cylindrical area 132 between the plane of the lower surface of the self-sealing injection site 10, the bottom of the annular space 130 and a plane across the outer opening of the cylindrical bore 96 are then backfilled by additional medical grade adhesive 114 as illustrated in FIG. 10A to fully and adhesively secure the self-sealing injection site 10 within the cylindrical bore 96 of the elastomeric shell 82.

It is to be understood that the annular space 130 arrangement and backfill space 132 represent a preferred embodiment of the mounting arrangement for placement of the injection sites and plugs of the invention in openings of various devices. A tight fit of the injection site or plug within such openings may be acceptable in many devices, the permanent placement being facilitated by adhesive or other bonding.

Figure 10A:
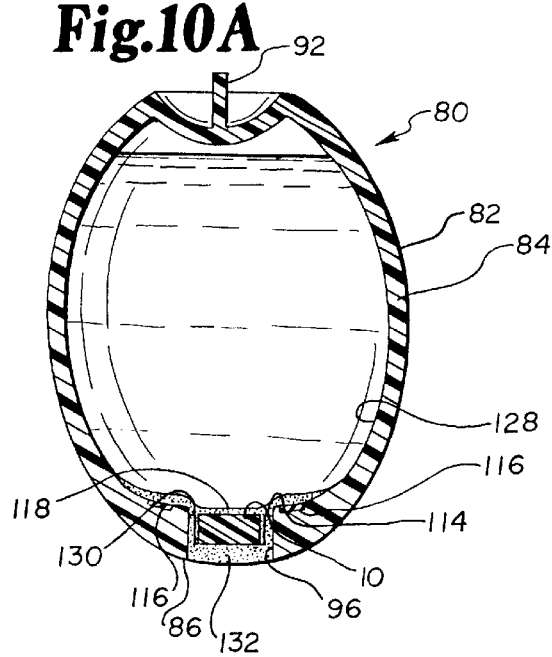
FIG. 10A illustrates complete encapsulation of the self-sealing injection site within the cylindrical bore of the elastomeric shell.

FIG. 10A illustrates the complete encapsulation of self-sealing injection site 10 within the cylindrical bore 96 of the elastomeric shell 82 containing a saline or other suitable biologically safe fluid 134 where all numerals correspond to those elements previously described. Backfilling with adhesive 114 of the cylindrical bore 96 in areas 130 and 132 forms a homogenous surroundment of adhesive 114 about the self-sealing injection site 10. The newly applied backfill adhesive of the same type provides for bonding of the previously cured adhesive and the newly applied adhesive to form a homogenous bonding.

The elastomeric shell 82 is of a medical grade low durometer silicone elastomer, thus allowing the elastomeric shell 82 to be soft and resilient. The self-sealing injection site 10 is also constructed of a low durometer medical grade silicone elastomer which has minimal palpability and which is easily compressed. The silicone adhesive 114 when cured and hardened has durometer and elongation qualities similar to the other silicone elastomeric members which it bonds together. The silicone adhesive 114 is biocompatable and biostable.

Also illustrated in this Figure is an annular area 116 for serialization and identification of the product.

Figure 10B:
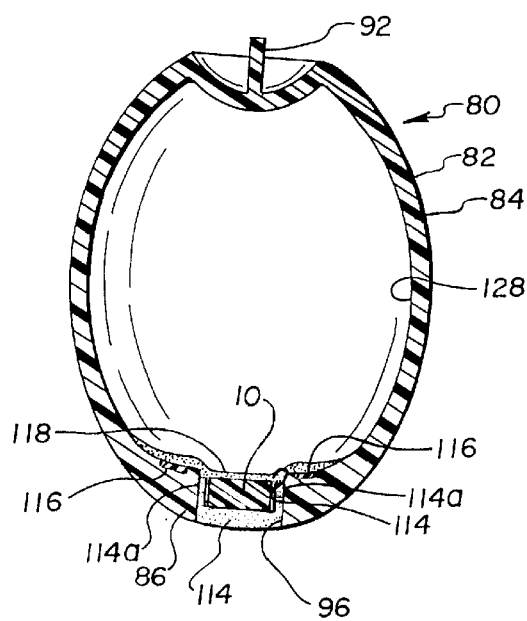
FIG. 10B illustrates radiopaque encapsulation of the self-sealing injection site.

FIG. 10B illustrates the complete encapsulation of a self-sealing injection site 10 incorporating a band of suitable radiopaque adhesive 114a containing barium sulfate (BaSo$_4$) in a range of 14% to provide for a radiopaque member surrounding the self-sealing injection site 10 in the upper portion of the annular area 130 of the cylindrical bore 96 surrounding the self-sealing injection site 10. Adhesive 114 is then backfilled into the area 132 of the cylindrical bore 96 about the remaining portion of the self-sealing injection site 10 and in direct adhesion with the barium sulfate laden adhesive 114a in the annular area 130 as was described in FIG. 10A. All numerals correspond to these elements previously described.

Figure 10C:
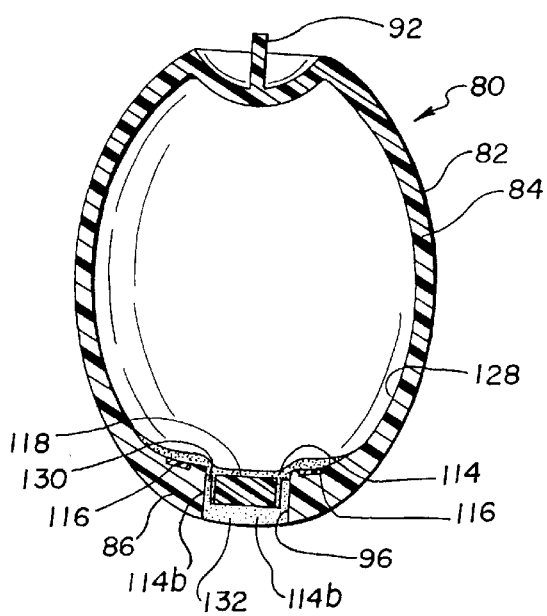
FIG. 10C illustrates encapsulation of the self-sealing injection site.

FIG. 10C illustrates the complete encapsulation of a self-sealing injection site 10 incorporating a band of suitable radiopaque adhesive 114b containing barium sulfate (BaSo$_4$) in a range of 14% to provide for a radiopaque member completely surrounding the self-sealing injection site 10 in the annular areas 130 and 132. Adhesive 114b is backfilled in the areas 130 and 132 of the cylindrical bore 96 in direct contact with the adhesive 114 to complete the encapsulation of the self-sealing injection site 10. All elements correspond to those elements previously described.

Figure 11:
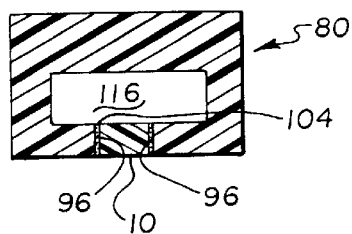
FIG. 11 is a schematic showing of a device depicted generally, making use of the invention.

Referring now to FIG. 11, a schematic showing of a generalized device 80 is depicted. Device 80 may be any device requiring a septum or plug 10 of the invention including any of the aforementioned devices or any other kind whether implantable of not. Such a device includes an opening 96 closed by an injection site or a plug 10 of the invention. Note that opening 96 does not include any supporting structured about it. In this embodiment, plug 10 fits tightly in opening 96 and may require only a thin layer of adhesive 104 to seal it therein. Such a fit may merely be an interference fit taking advantage of the continuous peripheral or circumferential surface of plug 10 for sealing engagement, of course as in other embodiments plug 10 is wrapped in tension.

While this invention may be embodied in many different forms, there are described in detail herein specific preferred embodiments of the invention. This description is an exemplification of the principles of the invention and is not intended to limit the invention to the particular embodiments illustrated.

Variations of the invention include but are not limited to colored injection sites for visualization, radiopaque sites for fluoroscopy and tailoring of the compressive loading by varying the diameter reduction in the rod when stretching it.

What is claimed is as follows:

1. A method of making a self-sealing injection site, said method comprising the steps of:

stretching an elastomeric body under tension from a non-deformed configuration to a deformed configuration;

placing a wrapping member around said elastomeric body; and releasing the tension on the elastomeric body, said wrapping member compressing said elastomeric body and preventing said elastomeric body from returning completely to said non-deformed configuration, thereby producing a self-sealing injection site.

2. The method of claim 1 wherein subsequent to the step of releasing the tension on the elastomeric body, the method includes the step of:

separating the elastomeric body into a plurality of discrete segments to form a plurality of like self-sealing injection sites.

3. The method of claim 1 wherein the wrapping member is a strand which is wound around at least a portion of the elastomeric body.

4. The method of claim 3 wherein the elastomeric body is an elongate rod having an outer surface, and the strand is wrapped spirally about said outer surface of said elongate rod.

5. The method of claim 3 further comprising the step of: applying adhesive to the strand such that at leasta portion of the strand bonds to the elastomeric body.

6. The method of claim 5 wherein the adhesive is applied to the strand prior to winding the strand on the elastomeric body.

7. The method of claim 3 wherein subseqiuent to the step of releasing the tension on the elastomeric body, the method comprises the step of:

slicing the elastomeric body and the wrapping member into segments to form a plurality of like self-sealing injection sites.

8. The method of claim 1 wherein the method further comprises the step of: applying adhesive to the wrapping member prior to winding the wrapping member around the elastomeric body.

9. The method of claim 8 wherein the elastomeric body is a rod having a generally circular cross-section.

10. The method of claim 8 further comprising the step of curing the adhesive prior to slicing the elastomeric body and the wrapping member into a plurality of like self-sealing injection sites.

11. A method of making a self-sealing injection site, said method comprising the steps of:

provicing an elastomeric core and a strand member, said elastomeric core having a length and an initial cross-sectional dimension;

applying tension to said elastomeric core to decrease said initial cross sectional dimension;

applying an adhesive to said strand member;

winding said strand member around said elastomeric core over at least a portion of said length thereof while said elastomeric body is under tension, said strand member forming a generally spiral configuration circumscribing said portion of said elastomeric core;

curing said adhesive;

relaxing the tension on said elastomeric core, said strand member compressing said elastomeric core and preventing said elastomeric core from returning completely to said initial cross sectional dimension; and cutting the elastomeric body and the strand member into at least one section corresponding to the self-sealing injection site, thereby producing at least one self-sealing injection site having an elastomeric core in a compressed configuration.

12. The method of claim 11 wherein the elastomeric core is cut into a plurality of segments to produce a plurality of like self-sealing injection sites.

13. The method of claim 11 wherein the elastomeric core has a generally round cross-section.

14. The method of claim 11 wherein the elastomeric core is silicone.

15. The method of claim 11 wherein the strand member is fiberglass.

16. The method of claim 11 wherein the strand member is polyester terephthalate.

17. The method of claim 11 wherein the strand member is wound spirally such that the strand member forms a series of generally parallel coiled loops extending along the portion of the elastomeric core.

* * * * *

UNITED STATES PATENT AND TRADEMARK OFFICE
CERTIFICATE OF CORRECTION

PATENT NO. : 5,935,362
DATED : August 10, 1999
INVENTOR(S) : Timothy B. Petrick

It is certified that error appears in the above-identified patent and that said Letters Patent is hereby corrected as shown below:

Column 10,
Line 47, insert a space between the words "least" and "a".

Signed and Sealed this

Eighth Day of March, 2005

JON W. DUDAS
*Director of the United States Patent and Trademark Office*